(12) United States Patent
Ranieri et al.

(10) Patent No.: US 8,128,923 B2
(45) Date of Patent: Mar. 6, 2012

(54) RENAL CARCINOMA CELL LINE AND USES THEREOF

(75) Inventors: Elena Ranieri, Bari (IT); Michele Battaglia, Bari (IT); Herr Wolfgang, Mainz (DE); Loreto Gesualdo, Altamura (IT)

(73) Assignees: Universita' Degli Studi Di Bari, Bari (IT); Universita' Degli Studi Di Foggia, Foggia (IT)

(*) Notice: Subject to any disclaimer, the term of this patent is extended or adjusted under 35 U.S.C. 154(b) by 744 days.

(21) Appl. No.: 12/083,842

(22) PCT Filed: Oct. 20, 2006

(86) PCT No.: PCT/EP2006/067631
§ 371 (c)(1),
(2), (4) Date: Apr. 18, 2008

(87) PCT Pub. No.: WO2007/045691
PCT Pub. Date: Apr. 26, 2007

(65) Prior Publication Data
US 2009/0136458 A1 May 28, 2009

(30) Foreign Application Priority Data
Oct. 21, 2005 (IT) .............................. MI2005A2018

(51) Int. Cl.
*C12N 5/09* (2010.01)
(52) U.S. Cl. ........................................ 424/93.7; 435/369
(58) Field of Classification Search .................. 435/369; 424/93.7
See application file for complete search history.

(56) References Cited

U.S. PATENT DOCUMENTS
2002/0119121 A1 * 8/2002 Vitiello et al. ............... 424/85.2

OTHER PUBLICATIONS
Banchereau et al. Dendritic cells and the control of immunity. Nature vol. 392, Mar. 19, 1998. p. 245-252.*
Lichtenfels et al. Identification of metabolic enzymes in renal cell carcinoma utilizing PROTEOMEX analyses. Biochimica et Biophysica Acta 1646 (2003) 21-31.*
Bear et al., "Characterization of two human cell lines (TK-10, TK-164) of renal cell cancer," *Cancer Research*, 47:3856-3862 (1987).
Hold et al., "Immunotherapy of metastatic renal cell carcinoma with tumor lysate-pulsed autologous dendritic cells," *Clinical Cancer Research*, 8:3369-3376 (2002).
van Spronsen et al., "Novel treatment strategies in clear-cell metastatic renal cell carcinoma," *Anti-Cancer Drugs*, 16:709-717 (2005).

* cited by examiner

*Primary Examiner* — Taeyoon Kim
(74) *Attorney, Agent, or Firm* — Medlen & Carroll, LLP

(57) ABSTRACT

The present invention relates to a renal carcinoma cell line capable of activating the immune system in an antigen-specific manner. According to a further aspect, the invention also includes derivatives of the cell line that maintain said activation capacity. The invention also comprises a method for targeting and activating immune system cells against cells of clear cell renal carcinoma. Said method comprises the co-incubation of isolated immune system cells (dendritic cells, CD4+, CD8+ lymphocytes etc.) with cells of the RCC BA85#21 line in accordance with the invention in a suitable culture medium, for a time sufficient to obtain antigen specific cells.

13 Claims, 7 Drawing Sheets

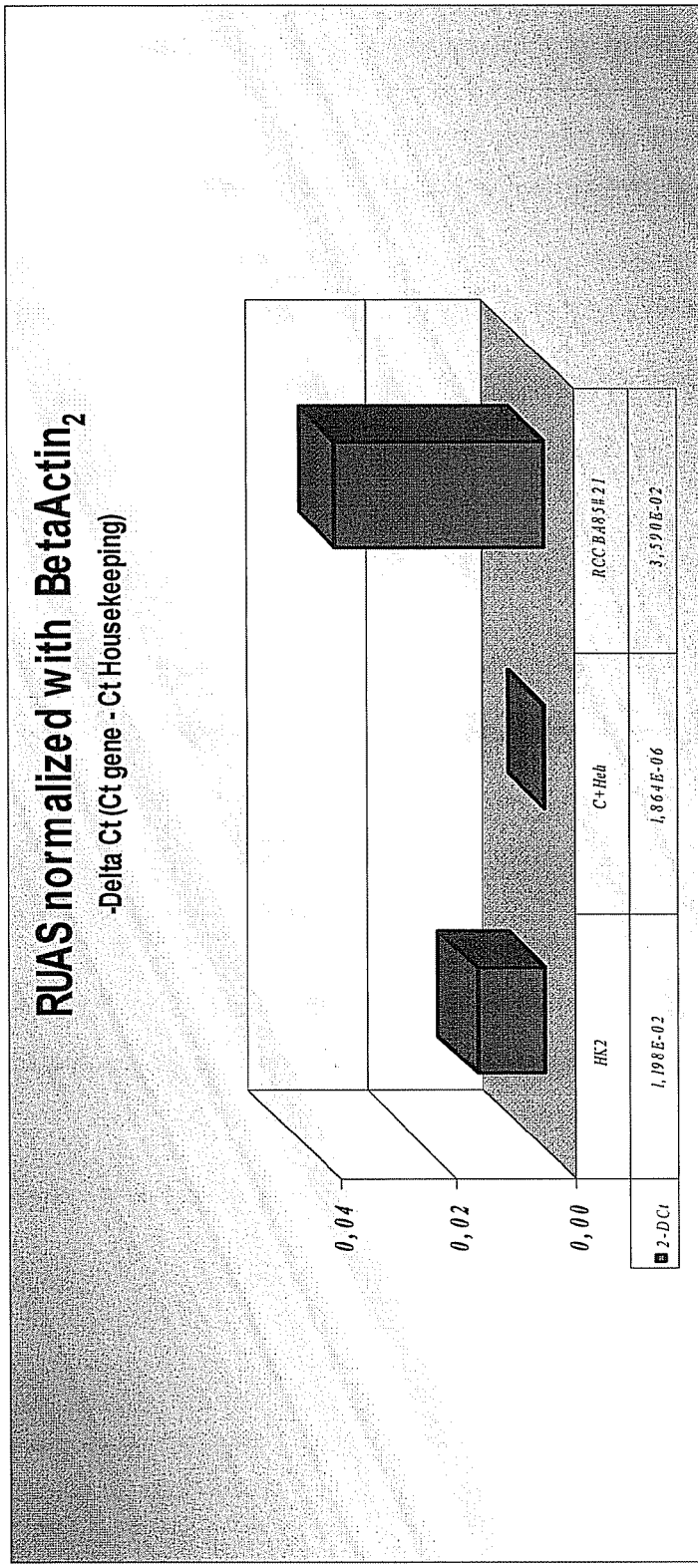

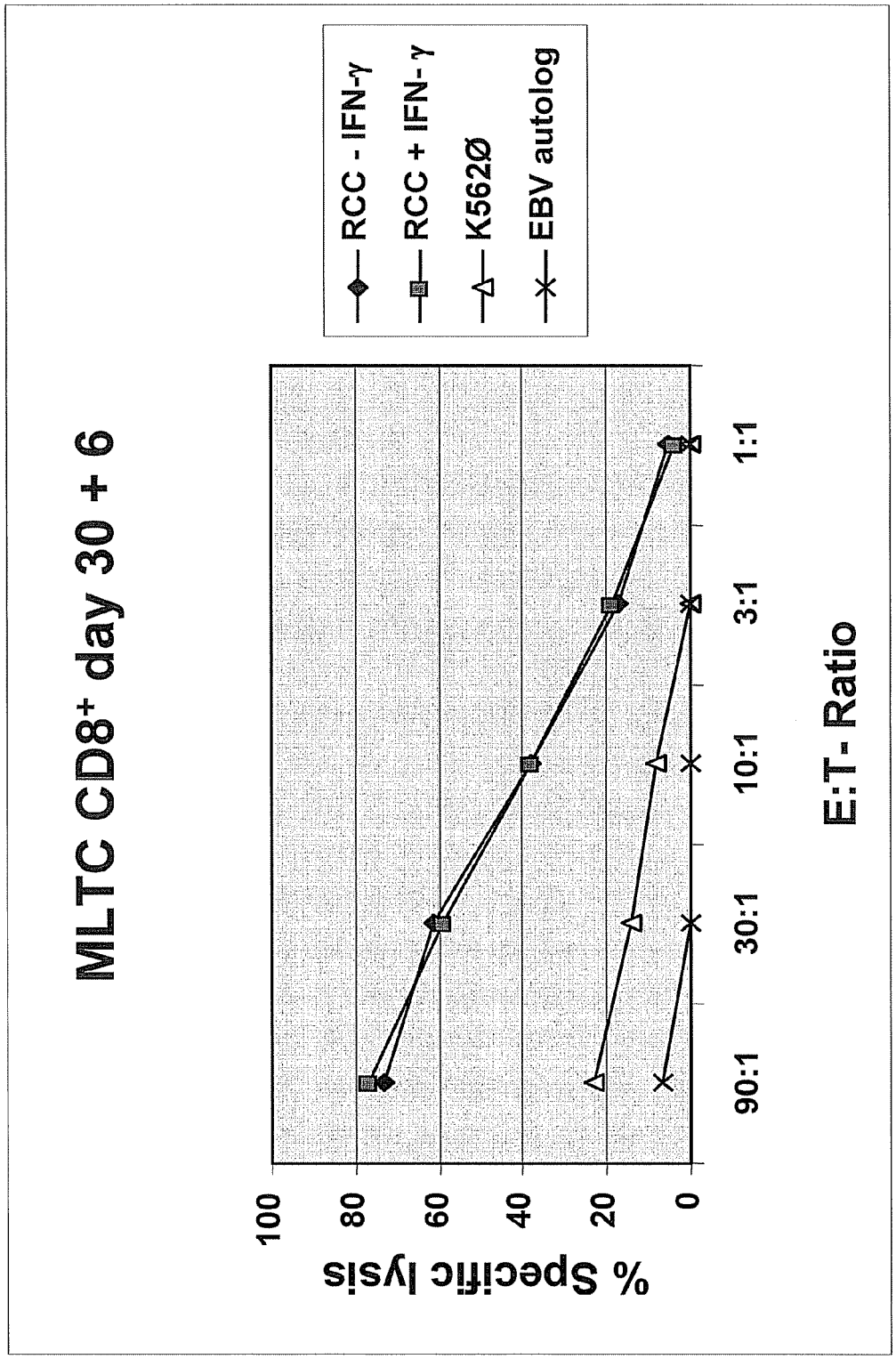

RENAL CARCINOMA CELL LINE AND USES THEREOF

Figure 1A:
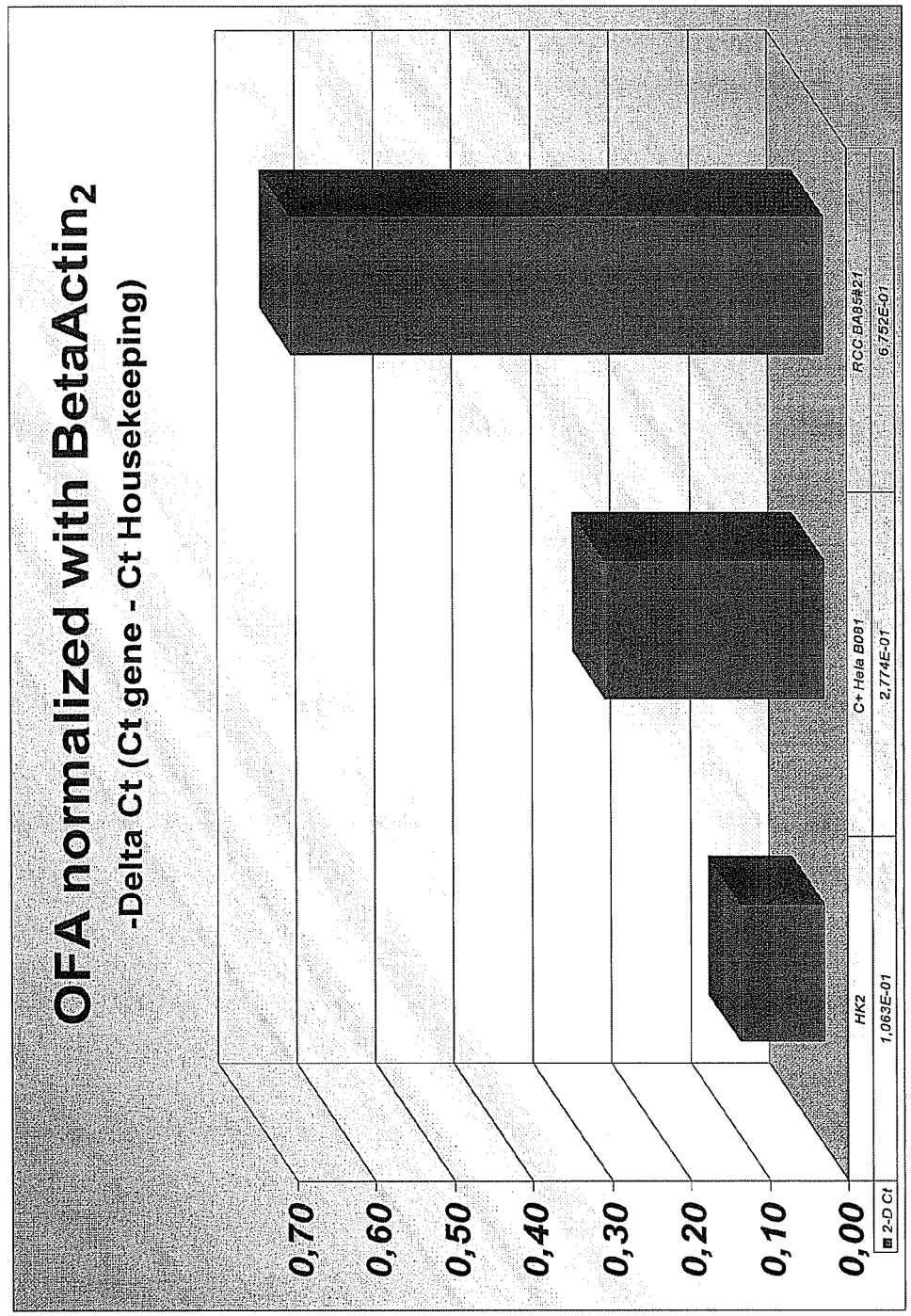
Figure 1B:
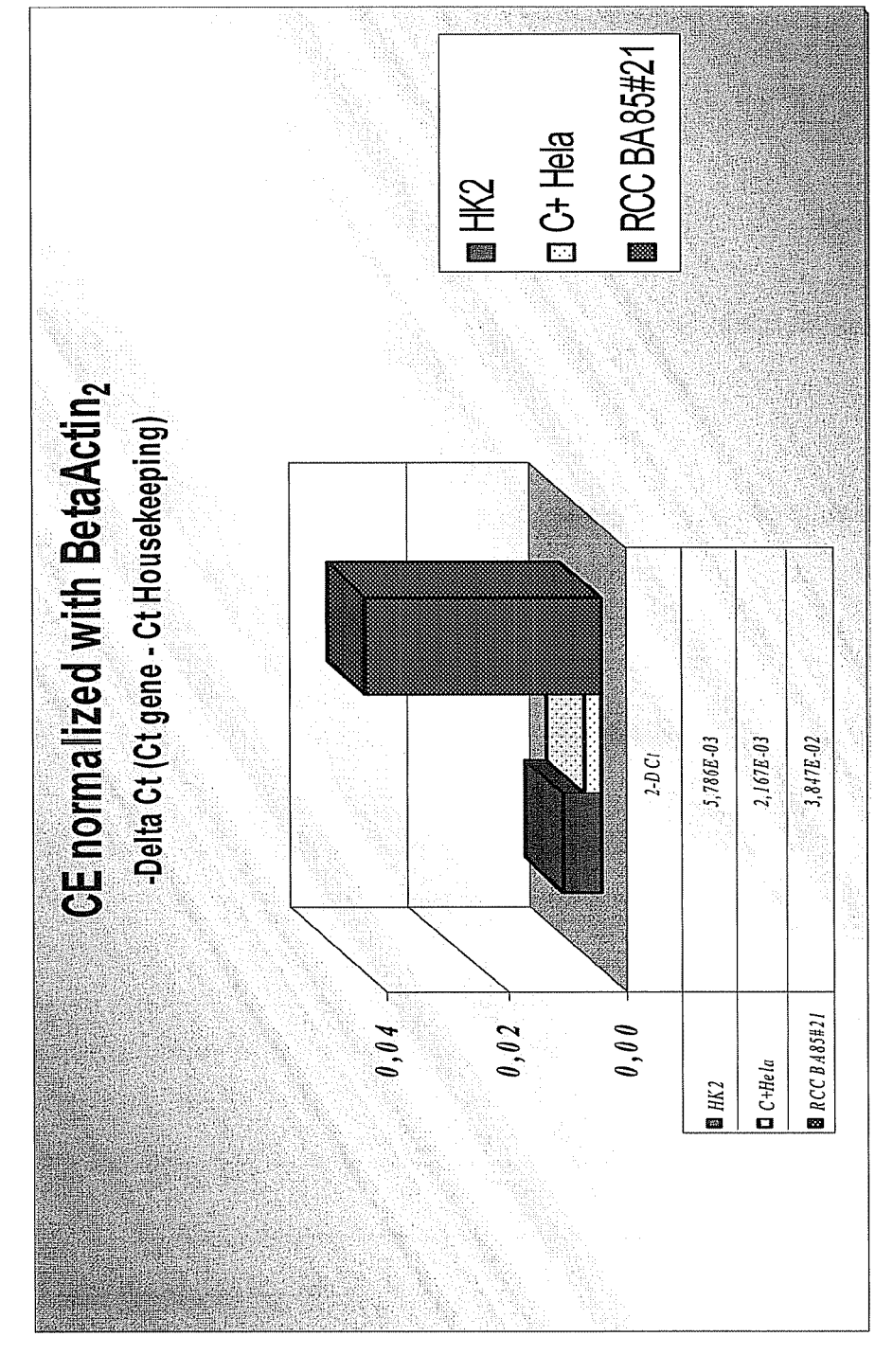
Figure 1C:
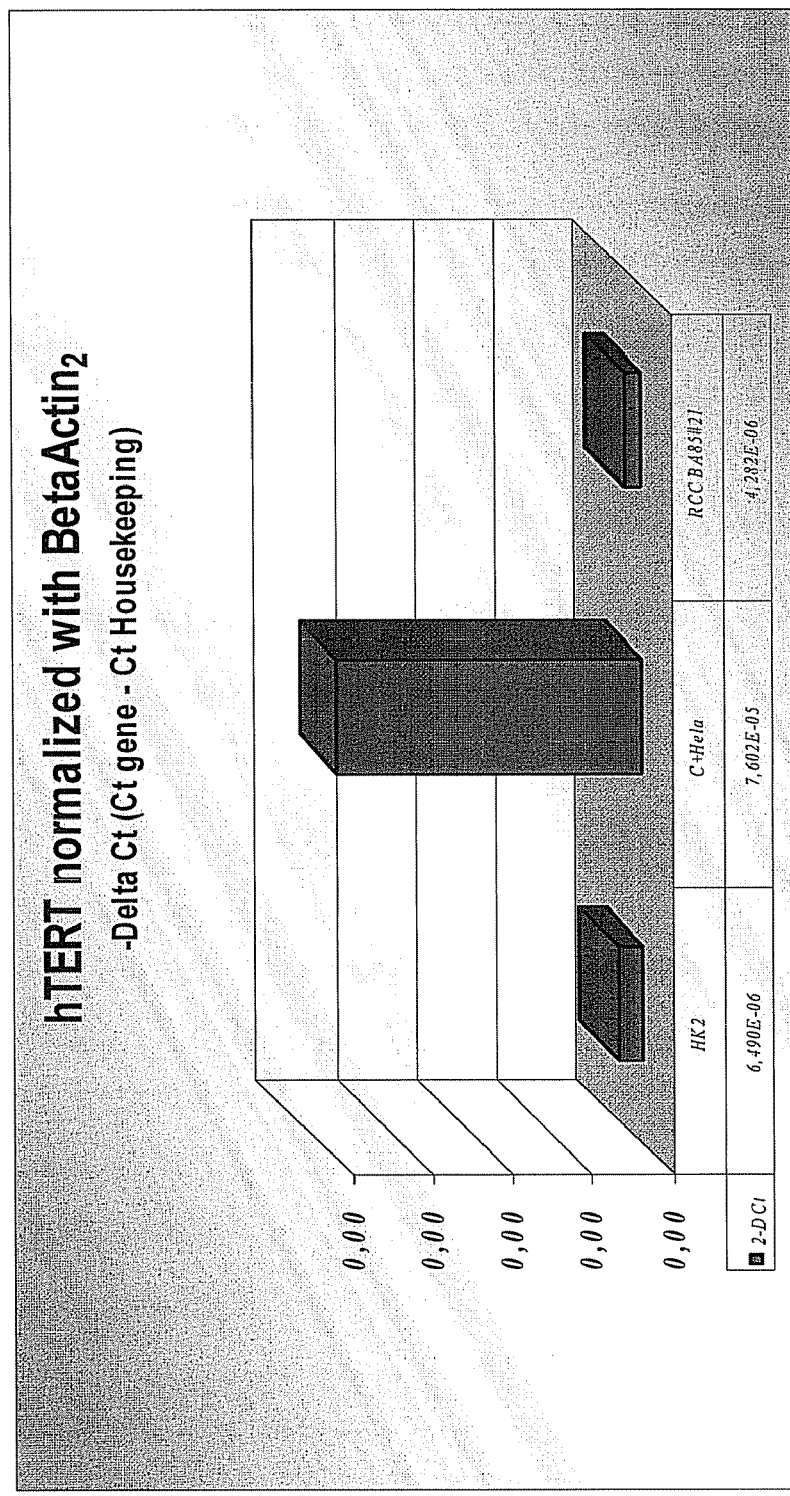
Figure 1E:
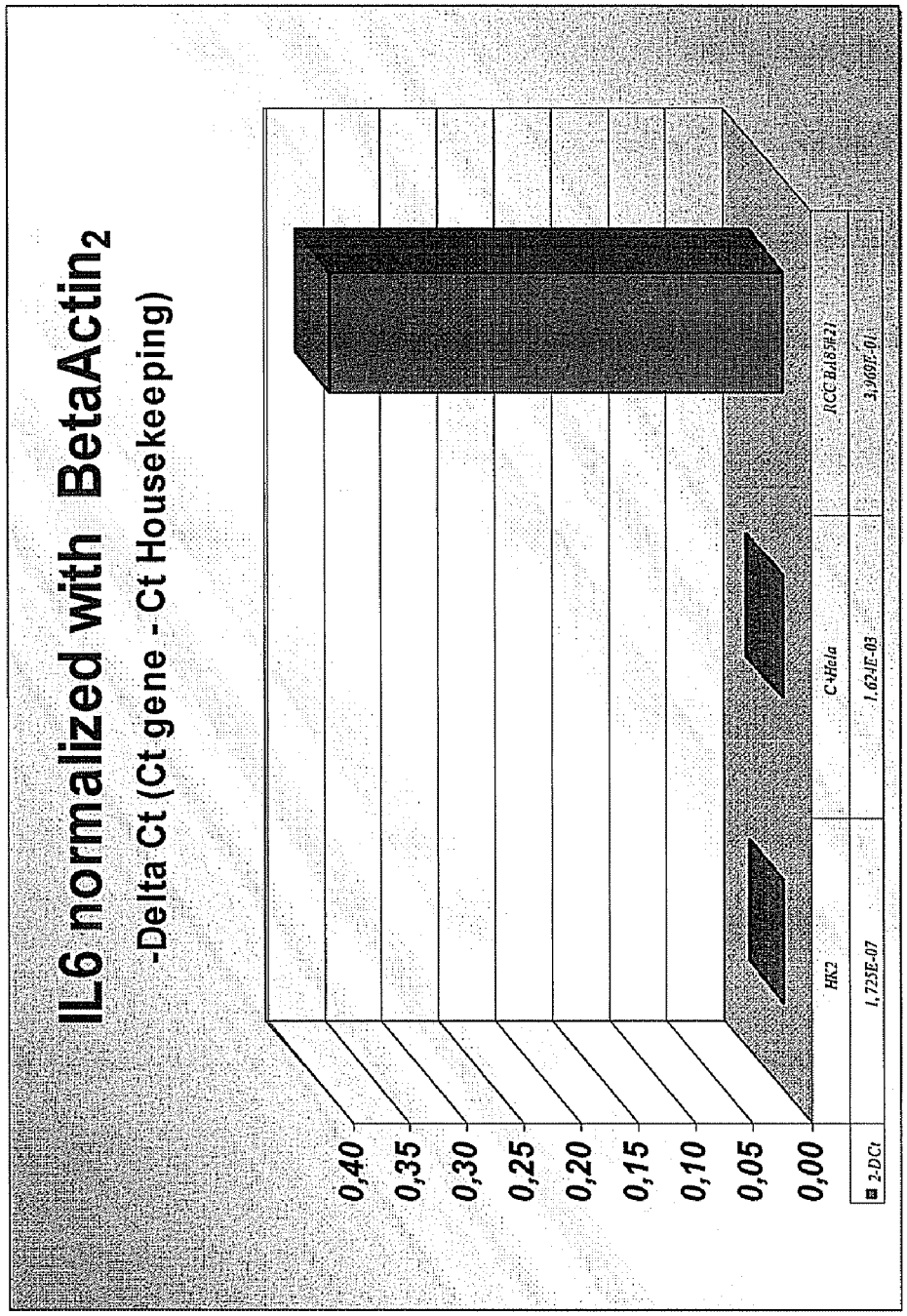

This application is a U.S. national entry of International Application No. PCT/EP2006/067631, filed Oct. 20, 2006, which claims priority to Italian Patent Application No. MI2005A002018, filed Oct. 21, 2005.

FIELD OF THE INVENTION

The present invention relates to a tumor cell line for use in the field of cellular therapy and/or prophylaxis.

PRIOR ART

Clear cell renal carcinoma (RCC) is the most common malignant neoplasia of the kidney, accounting for about 3% of malignant neoplasias in adults with about 30,000 new cases diagnosed each year in the United States and 27,000 in Europe, and 95,000 deaths per year world-wide (Bander N H, et al. Cancer Res. 1989 Dec. 1; 49(23):6774-80). Each year in Italy, renal neoplasia affects 4000 people causing 200 deaths. It is the third most common type of urological tumor after prostate and bladder tumors, appearing to have a preference for the male sex (2:1 male/female ratio) and with an incidence peak around the sixth to seventh decade of life. Unfortunately, its etiology is not known.

RCC is a disease curable only in early diagnosed cases and hence treatable by radical surgery. RCC presents a neoplastic cellularity which is very resistant to traditional chemotherapy regimens and relatively resistant to conventional radiotherapy. To date, chemotherapy in patients with metastatic RCC has not yielded satisfactory results. Recent data have shown that in 3000 cases of patients on chemotherapy, only 5% have responded to the therapeutic regimen. These results show that RCC is highly resistant to a range of chemotherapeutic agents administered either in combination or not in combination, indicating a need for new agents and new therapeutic methods.

RCC is one of a small group of malignant neoplasias in which an antigen-specific and cell-mediated anti-tumor immune response has been demonstrated. This fact suggests that the carcinoma expresses antigens recognisable by the immune system, particularly by cytotoxic T-lymphocytes (CTLs), and which can enable the development of a tumor-rejection-type immune response. Developing strategies for CTL type anti-tumor immunization is secondary to identifying tumor antigens recognised by CTLs in renal tumor cell lines, and cells able to efficiently present the antigen to the immune system, such as dendritic cells.

Currently, the main difficulty lies with identifying and selecting a highly immunogenic antigen format for use as a source of new renal tumor antigens to prime dendritic cells (DC) used as an immunotherapeutic approach, for enhancing the immune response in patients compromised by neoplastic pathology.

To date, isolation of stable renal tumor lines remains an infrequent occurrence, although renal tumor cells have been isolated and cultivated in vitro by several laboratories over the last 30 years (Bander N H, et al. Cancer Res. 1989 Dec. 1; 49(23):6774-80; Bear A, et al. Cancer Res. 1987 Jul. 15; 47(14):3856-62; Blouin P, et al. Exp Pathol. 1989; 36(3):147-63). The immunogenicity of renal tumor lines still remains a characteristic that is not always present, despite the fact that for other tumor types of varying histology (melanoma, pancreatic carcinoma, prostate carcinoma, mesothelioma, hepatocarcinoma and renal carcinoma), laboratory isolated cell lines are already utilized for preparing vaccines based on the use of DCs for inducing an antigen-specific response. Data obtained from these studies have proved promising for a future use of tumor cells for immunotherapy in individuals affected by solid tumors, despite percentage response to the vaccine being highly variable. In any event, the degree of immunogenicity of the isolated tumor lines remains a critical parameter in formulating a vaccine for treating solid neoplasias.

SUMMARY

The present invention relates to a cell line of clear cell renal carcinoma, named RCC BA85#21 and deposited as number PD 04006 at the CBA in Genoa (Italy). The cell line is capable of activating the immune system in an antigen-specific manner. In accordance with a further aspect, the invention also relates to derivatives of the cell line that maintain said immune system activation capacity.

The invention also comprises a method for activating cells of the immune system and specifically targeting them to recognize renal carcinoma cells, preferably clear cells. Said method comprises the co-incubation of isolated cells of the immune system (dendritic cells, lymphocytes, $CD4^+$, $CD8^+$, etc) with cells of the RCC BA85#21 line in a suitable culture medium for a time sufficient to obtain antigen specific cells.

DETAILED DESCRIPTION OF THE FIGURES

FIG. 1: Evaluation of the gene expression of the tumor markers: OFA (FIG. 1a), CE (FIG. 1b), hTert (FIG. 1c), RUAS (FIG. 1d) and interleukin-6 (FIG. 1e) of the RCC BA85#21 clone with Real Time PCR.

Figure 2:
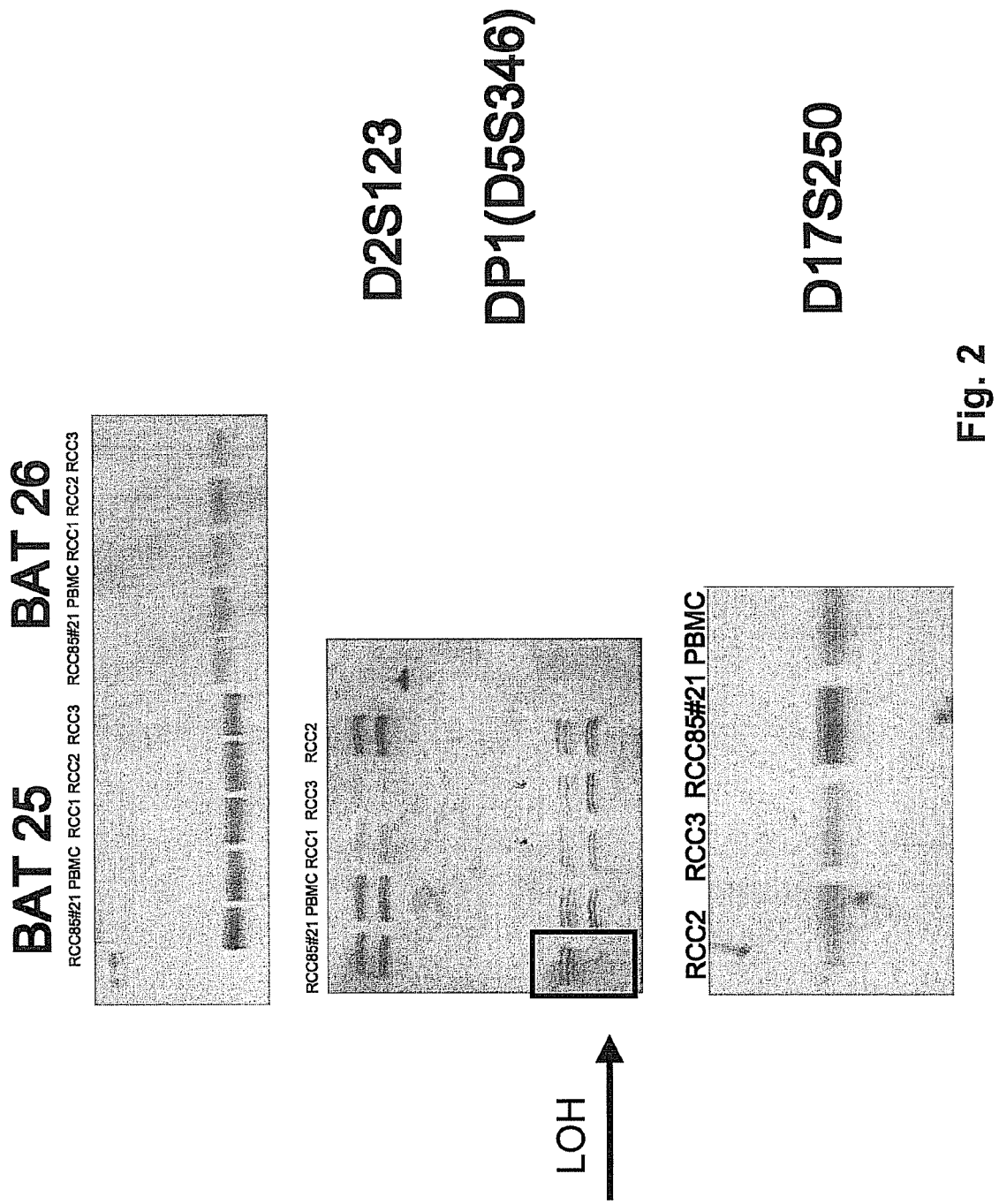

FIG. 2: Microsatellite Instability (MSI) and loss of heterozygosity (LOH) in control lymphocyte (PBMC) and in the RCC 85 clone at different passages (Mother line BA85 RCC1=1, Mother line BA85 RCC2=2, Mother line BA85 RCC 3=3). Tested loci: BAT25 and BAT26, DS123 and DP1 (D5S346), D175250. LOH is present only in the RCC 85#21 clone at the DP1 locus.

FIG. 3: Cytotoxicity tests of $CD8^+$ autologous T-lymphocytes against the RCC BA85#21 clone (60% lysis, E/T=60:1). Non-specific lysis of the erythroid cell line K562 is found to be less than 20%.

DETAILED DESCRIPTION OF THE INVENTION

The present invention relates to the isolation, characterization and use of a human cell line derived from a clear cell renal tumor having been phenotypically and functionally characterized in the present invention.

The renal tumor cell clone was isolated from a primary lesion of clear cell renal carcinoma and deposited at the CBA (Advanced Biotechnology Center) in Genoa on 17 Dec. 2004 as deposit number PD04006. In the present study the cell line was denominated RCC BA85#21.

The availability of said cell line, characterized (the principle characteristics are given in Table 1) and possessing high immunogenicity, enables:

the identification of new tumor antigens,
the standardization of somatic therapy based on the use of autologous dendritic cells primed with the immunogenic tumor cell line lysate, with Class I and II peptides derived from the identified tumor antigens or with the antigen itself, capable of promoting the activation and expansion of specific T cells against renal tumor cells in patients affected by RCC.

The RCC BA85#21 cell line can be optionally transformed with heterologous nucleic acids. The transformation is implemented with methods known in the art and can be undertaken to provide the cells with antibiotic resistance, an additional antigenic characteristic or an easily selectable characteristic.

Hence cells obtainable from the original cell line by transformation with heterologous nucleic acids fall within the scope of the present invention. The same applies to clonal derivative cells, which after treatment in culture of the RCC BA85#21 with various factors, such as growth factors and/or cytokines, are shown to have the capacity for activating the immune system or immune system cells or to have growth characteristics particularly suited to the activities required for the purposes of the present invention.

The principal characteristic of said cells is their immunogenicity, measured as their capacity for stimulating an antigen-specific response in the cells of the immune system. A specific response means a response (demonstrable by the production of signal mediators such as cytokines or by the activation of other cell types, or by flow cytometry) which is greater than a response identifiable as control.

The invention also comprises products derived from the RCC BA85#21 cell line obtainable after culturing a suitable quantity of cells, preferably in RPMI 1640 medium with added fetal serum or insulin (20 µg/ml), transferrin (10 µg/ml), sodium selenite (25 nM), hydrocortisone (50 nM), EGF (1 ng/ml), ethanolamine, (10 µM), phosphorylethanolamine (10 µM), triiodotyronine (100 pM), bovine serum albumin (2 mg/ml), HEPES buffer (10 mM), glutamine (2 mM) and sodium pyruvate (0.5 mM), then concentrating the cell fraction for example by centrifugation or filtration, or by fixing (such as treatment with dialdehydes) or by irradiation with preferably γ rays, lyophilization and/or freezing.

Derivates of said cell line are also obtained from the RCC BA85#21 cell clone for example by cell lysis and/or fractionation and/or lyophilization and/or apoptotic body preparation etc. Said derivates, at least partially containing the protein fraction of the original clone and hence also the specifically expressed renal carcinoma antigens, totally or partially retain the immunogenic qualities of the RCC BA85#21 clone and can be used as a replacement therefor.

The cell line of the invention is used with the aim of inducing and/or increasing the immune response for therapeutic and/or prophylactic purposes by isolating genetically transformed cells, or by preparing lysates or apoptotic bodies.

Said extracts, fractions and/or cell preparations and combinations thereof in various proportions can be suitably mixed with excipients, diluents and/or stabilizers in pharmaceutical or immunogenic compositions.

The invention therefore includes compositions comprising variously treated RCC BA85#21 cells and/or derivatives thereof, usable for inducing a specific immunogenic response in immune system cells, preferably lymphocytes and/or dendritic cells. Said compositions are used for pharmaceutical and/or vaccination purposes in the preparation of medicaments for prophylaxis and/or therapy of renal carcinoma.

Methods for activating and targeting immune response effectors such as cells of the immune system, particularly T-lymphocytes and even more preferably CD8+ cells, specific for clear cell renal carcinoma cells such as those of the present invention and/or their derivatives, comprise the co-incubation of immune system cells, preferably lymphocytes or dendritic cells, with cells of the RCC BA85#21 line or with its derivates as aforedefined. Said co-incubation is preferably effected in a suitable culture medium such as RPMI 1640 with added human AB+ serum and/or growth and/or activation factors (e.g. cytokines) for a time sufficient to obtain antigen-specific cells. In vitro methods for lymphocyte activation are known in the art: (cultivation of tumor cells, irradiation with γ rays, in vitro lymphocyte stimulation, i.e. co-culturing previously inactivated tumor cells and lymphocytes, evaluation of lymphocyte induction/activation by Elispot assay for IFN-γ, cytotoxicity assay, phenotypical evaluation of lymphocytes via flow cytometry, evaluation of lymphocyte proliferation in response to tumor antigen). In accordance with a preferred aspect, the cells of the invention are used for priming dendritic cells, for activating CD4+/CD8+ lymphocytes and natural killer cells, and for inducing an antigen-specific response restricted to the HLA-A and B/C alleles and not HLA restricted.

The specificity of response induced in lymphocyte cells by the cells of the invention is measured by methods known in the art, such as cell proliferation after co-incubation of the two cell types, production of cytokines or growth factors, appearance of particular surface antigens such as: OFA (oncofetal antigen), carboxylesterase (CE), RUAS and hTERT (human telomerase reverse transcriptase).

Therefore, in accordance with a preferred embodiment, the cells and derivatives of the invention are used in in vitro, ex vivo and in vivo immunotherapy protocols in which the lymphocytes or immune system cells of a patient suffering from kidney tumor, preferably clear cell (RCC), are stimulated in vitro with a cell culture of the RCC BA85#21 line or with its derivatives under suitable conditions, such as those detailed in Oosterwijk-Wakka J C, J Immunother. 2002; 25(6):500-8 and in Holtl L. et al. Clin Cancer Res. 2002 November; 8(11):3369-76 and also in Gitlitz B J, et al. J Immunother. 2003; 26(5):412-9, then re-introduced into the patient optionally after a selection passage also undertaken in vitro, for example by immunochemical methods.

In accordance with a further aspect, the invention hence comprises the use of the RCC BA85#21 cell line to prepare a vaccine for the treatment and/or prevention of renal neoplasias, specifically clear cell renal neoplasia, or to stimulate immune system cells in vitro, preferably lymphocytes and/or antigen-specific dendritic cells. The RCC BA85#21 cell line is also an essential instrument in the selection and purification of specific antigens expressed in renal tumors. Therefore, in accordance with this use, the cell line is grown and amplified, optionally further treated, for example lysed, then studied using analytical methods for characterizing surface or cellular antigens. Methods for characterizing specific antigens are for example electrophoresis, preferably bidimensional electrophoresis, electrofocusing or immunoelectrofocusing, metabolic marking followed by immunoprecipitation etc. The invention hence comprises the use of the RCC BA85#21 cell line for selecting and purifying, for both analytical and preparative purposes, antigens specific for renal carcinoma preferably of clear cell type.

In accordance with a further aspect the invention relates to a diagnostic method for renal carcinoma which comprises checking the presence of a tumor antigen panel including, among numerous others, the following antigens: TP53TG3 (Tumor Protein 53 Target Gene 3); Trafficking protein particle complex 1 (TRAPPC1) (involved in the transport from endoplasmic reticulum to Golgi); Trafficking protein particle complex 2 (TRAPPC2/SEDLP) (involved in skeletal development, transcription and regulation of DNA-dependent transcription, transport from endoplasmic reticulum to Golgi); Trafficking protein particle complex 2 (TRAPPC2) (involved in spondyloepiphyseal dysplasia, tarda); Trafficking protein particle complex 3 (TRAPPC3) (involved in the transport from endoplasmic reticulum to Golgi); Trafficking protein particle complex 4 (TRAPPC4) (involved in the transport from endoplasmic reticulum to Golgi, vesicular transport, dendritic morphogenesis, biosynthesis of neurotransmitter receptors); Trafficking protein particle complex 5 (TRAPPC5); Trafficking protein particle complex 6 (TRAPPC6). This check is undertaken with methods that show the presence of the protein product or specific RNA, thus either by immunochemical methods using antibodies or by molecular methods using probes and molecular seeds.

In accordance with a further aspect, the invention relates to a kit comprising the RCC BA85#21 cell line, preferably in the form of a centrifuged pellet, or in frozen and/or lysed and/or lyophilized form, or derivatives thereof in combination with or without reagents (such as growth media and/or cytokines) for preparing vaccine or immunogenic compositions, useful for implementing in vivo and/or ex vivo immunotherapy protocols, or to induce an antigen specific immune response in cells of the immune system.

EXPERIMENTAL PART

Example 1

Isolation, Culture and Morphological Characterization of the RCC BA85#21 Clone of Renal Tumor Cells The RCC BA85#21 renal tumor cell line (Elthem) was isolated from the primary tumor site of a patient affected by clear cell renal carcinoma after obtaining the informed consent of the donor. The primary tumor from which the RCC BA85#21 cell line was isolated was of histological grade 1 (according to Fuhrman as defined in Fuhrman S A et al. Am J Surg Pathol, 6(7): 655, 1982), non-aggressive, in which respect it had not invaded the renal artery or vena cava and had not metastasised the nearby lymph nodes. The tumor tissue of the primary lesion was composed principally of clear cells with alveolar/tubular arrangement.

The resected tumor tissue was finely cut up to obtain fragments of 1-2 mm in length. The tissue thus obtained was transferred into a sterile bottle containing 35 ml of PBS at pH 7.4 to which were added 5 ml of hyaluronidase (0.1%), 5 ml of collagenase IV (1%) and 5 ml of DNase (0.02%) for 20-30 minutes at room temperature. The cell suspension was filtered (100 μm Falcon 2350 strainer) and the cells washed several times in a balanced saline solution (HBSS). The supernatant was discarded, the pellet resuspended in culture medium and the cells placed in a 25 cm² flask. The cells were initially cultured in ACL-4 medium supplemented with 20% bovine serum (AR5). The AR5 medium was composed of RPMI 1640 medium with added insulin (20 μg/ml), transferrin (10 μg/ml), sodium selenite (25 nM), hydrocortisone (50 nM), EGF 1 ng/ml), ethanolamine (10 μM), phosphorylethanolamine (10 μM), triiodotyronine (100 pM), bovine serum albumin (2 mg/ml), HEPES buffer (10 mM), glutamine (2 mM) and sodium pyruvate (0.5 mM).

The cells were then cultivated in RPMI medium supplemented with 20% FCS, L-glutamine (216 mg/ml), penicillin (100 IU/ml), streptomycin (100 mg/ml) and HEPES (10 mM). The cells were frozen in 10% DMSO in HSA (human serum albumin).

The cells of the RCC85 line were cloned by the limiting dilution technique. Tumor cells at passage P 39 at $1\times10^5$ concentration were diluted in RPMI 1640 medium with added 20% FCS, 1% L-glutamine, 1% penicillin-streptomycin and plated into 96-well plates. $1\times10^4$ "feeder cells" (NIH 3T3) irradiated at 10,000 rad were added to the culture wells in the ratios given below.

| Cells/w | VOLUME/ml | FEEDER | Tumor cells/w |
|---|---|---|---|
| 96w-plates (U-bottom) | 100 μl | $4 \times 10^4$ | $3 \times 10^3$ |
| 48w- plates | 1 ml | $1 \times 10^5$ | $2.5 \times 10^4$ |
| 24w- plates | 2 ml | $2 \times 10^5$ | $5 \times 10^4$ |

The final result was the isolation of a stabilized and immunogenic clone of renal tumor cells, namely the RCC BA85#21 clone, presenting as homogeneous in cell shape (polygonal) and polynucleate with nuclei positioned centrally in the cytoplasm, and with tendency to alveolar cluster formation; also presenting eosinophilia with obvious glycogen and lipid deposits when stained with standard hematoxylin-eosin. The principle characteristics of the clone are given in table 1.

TABLE 1

| Renal carcinoma | RCC BA85#21 |
|---|---|
| Age/sex | 62/M |
| Size | 10 cm |
| Histological grade | 1 |
| Cytology | clear cells |
| Invasion of artery/vein | No |
| Metastasis of lymph nodes | T3aN0M0 |
| Number of passages | 50 |
| Duplication time | 72 hours |
| Cell contour | flat |
| Nuclei | polynucleate |
| Cell appearance | polygonal |

Example 2

Immunohistochemical Characterization of the RCC BA85#21 Clone

Monolayer cell preparations were obtained using ThinPrep apparatus (Cytyc Corp.). Cells were stained according to Papanicolaou and with immunohistochemical stains, undertaken with the Avidin-Biotin-Peroxidase (ABC) technique in an automated immunostainer (Dakocytomation, Carpinteria, Calif.—USA) using the following primary antibodies: CD 10 (Novocastra, Newcastle Upon Tyne—UK; clone: 56C6, 1/50 dilution); Cytokeratin AE1/AE3 (Dakocytomation; clone: AE1/AE/3, 1/5 dilution); Cytokeratin CAM 5.2 (Becton Dickinson, Franklin Lakes, N.J.—USA; clone: CAM 5.2, 1/2 dilution); Cytokeratin 19 (Dakocytomation; clone: BA17, 1/100 dilution); Epidermal Growth Factor receptor (EGF-R) (Dakocytomation; clone: H11, 1/50 dilution); Epithelial Membrane Antigen (EMA) (Dakocytomation; clone: E29, 1/100 dilution): Ki 67 (Dakocytomation; clone: MIB 1, 1/100 dilution); Mitochondria (Dakocytomation; clone: 113-1, 1/75 dilution); Vimentina (Dakocytomation; clone: V9, 1/2 dilution).

The histological preparations were incubated with the primary antibodies for 16 hours at 4° C., then with biotinilated secondary antibodies and with avidin-peroxidase for 30 minutes at 37° C. Chromogenic detection was undertaken with diaminobenzidine (DAB) for 20 minutes at 20° C. and nuclear contrast was obtained by immersing for 2 minutes in Meyer's hemalum. The sections were finally mounted with glycerinated gelatin on suitable coverslips. The results are shown in table 2.

TABLE 2

Positivity of the RCC BA85#21 cell line to epithelial markers

| Marker | RCC BA85#21 |
|---|---|
| CK19 | 25% |
| CKAE1/AE3 | 40% |
| CKCAM 5.2 | 99% |
| EMA | 5% |
| Vimentin | 99% |
| EGF-R | 30% |
| CD10 | Neg |
| Mitochondria | 99% |
| KI-67 | 4% |

The results obtained confirmed the tumor phenotype and the epithelial origin of the clone. To note is that the immunohistochemical analysis was undertaken on cells not treated with trypsin so as not to alter membrane antigens and consequent specific binding to the antibodies used for immunostaining. The markers used such as cytokeratin CAM 5.2, mitochondrial marker and vimentin proved to be strongly positive (99% of cells showed positivity), while cytokeratin AE1/AE3, cytokeratin 19, EGF-R, EMA and Ki 67 were positive though at lower percentages (positivity values from 4 to 40%). In conclusion the RCC cell line was found to be positive for the characteristic markers of neoplasia of epithelial origin such as cytokeratin CAM 5.2, mitochondrial markers, vimentin, cytokeratin AE1/AE3, cytokeratin 19, EGF-R, EMA and Ki 67, while CD 10 was found to be negative.

Example 3

Phenotyping of the RCC BA85#21 Clone by Flow Cytometry and Real Time PCR

The RCC BA85#21 clone was phenotyped with a panel of monoclonal antibodies (anti-MHC-I, anti-MHC-II, anti-CD40, anti-CD80, anti-CD54) in the presence or absence of stimulation with IFN-γ (500 IU/ml). The cells were analysed with a Partec flow cytofluorometer (Muenster, Germany).

The clone was found to be positive for class I, CD40 and CD54 molecules. The clone showed a low percentage of positivity for class II histocompatibility antigens and for the costimulatory molecule CD80, at both baseline conditions and after stimulation with IFN-γ. The results are summarized in table 3.

TABLE 3

Phenotypical characterization of the RCC BA85#21 clone by flow-cytometry.

| RCC BA85#21 | % baseline | % + IFN-γ |
|---|---|---|
| HLA-I | 99.8 | 99.9 |
| MFI | 8.60 | 28 |
| HLA-II | 1.16 | 2.35 |
| MFI | 1.63 | 1.17 |
| CD40 | 28 | 89.5 |
| MFI | 1.58 | 2.02 |
| CD80 | 0.45 | 0.96 |
| MFI | 2.50 | 1.38 |
| CD54 | 7.53 | 32.7 |
| MFI | 2.70 | 4.16 |

MFI = Mean fluorescence intensity

The percent values indicate the number of cells positive for the receptor studied; MFI is the fluorescent signal intensity correlating to the number of receptors per cell.

Gene expression of some tumor antigens and/or cytokines in RCC BA85#21 cells, in particular OFA (oncofetal antigen), carboxylesterase (CE) and RUAS, hTERT (human telomerase reverse transcriptase) and IL-6 has been checked by means of Real Time PCR, using double modified oligonucleotides and specific primers as described for example in Su Z. et al. Cancer Res., 2003 May 1; 63(9):2127-33. The results, normalized to the expression of a housekeeping gene, beta-actin, are shown in FIGS. 1a-1e. The absolute values were found to be: OFA ($2^{-\Delta CT}$=6.752E-01), hTERT ($2^{-\Delta Ct}$=4.282E-06), CE ($2^{-\Delta Ct}$=3.847E-02), RUAS ($2^{-\Delta Ct}$=3.590E-02) and IL-6 ($2^{-\Delta Ct}$=3.969E-01).

Example 4

Characterization of Genomic Stability of the RCC BA85#21 Clone

Genome stability of the RCC clone was assessed by analysis of microsatellite instability (MSI) and loss of heterozygosity (LOH) using PCR with primers for the loci BAT25 and BAT26 and for D2S123, D5S346 and D17S250 as described in Rodriguez-Bigas M A et al. J Natl Cancer Inst 1997; 89:1758-62 Boland C R. et al. Cancer Res 1998; 58:5248-57 and recommended by the National Cancer Institute Workshop. The PCR pattern, following vertical electrophoresis in polyacrylamide containing urea at 8M concentration, was compared to that of autologous lymphocytes (PBMC) and is shown in FIG. 2 (RCC1,2,3).

The PCR results show that, compared to the control, no MSI was found in the RCC BA85#21 clone. Instead, LOH was observed on locus DP1 or D5S346. The minimal region of deletion on 5 q which marks for LOH is mapped to locus 5q31.1 (interferon regulatory factor-1; locus IRF-1) in 23% of RCC cases. Data reported in the literature suggest that the LOH on 5 q plays an important role in the genesis of RCC, this genetic event being found in the initial phase of carcinogenesis (stages 2, 3, 4) (Ref. Sugimura J et al., Pathol Int. 1997; 47(2-3):79-83).

Example 5

Characterization of the RCC BA85#21 Clone by Microarray

Microarray analysis completed the phenotypical and functional framework of the RCC BA85#21 clone. The cRNA fragment was hybridized to a HG-U133Av2 oligonucleotide microarray microchip (Affymetrix) containing 22,283 gene sets, representing around 12,357 human genes and approximately 3,820 EST sequences with unknown function (Affymetrix Inc, Santa Clara, Calif.). For the data analysis, gene sets involved in the principle biological processes were selected: cell proliferation and cell cycle, apoptosis, cell angiogenesis and signalling, in accordance with the gene ontology database available at the NetAffx™ Analysis Center.

Among others the following markers were identified: TP53TG3; Trafficking protein particle complex 1 (TRAPPC1) (involved in the transport from endoplasmic reticulum to Golgi); Trafficking protein particle complex 2 (TRAPPC2/SEDLP) (involved in skeletal development, transcription and regulation of DNA-dependent transcription, transport from endoplasmic reticulum to Golgi); Trafficking protein particle complex 2 (TRAPPC2) (involved in spondyloepiphyseal dysplasia, tarda); Trafficking protein particle complex 3 (TRAPPC3) (involved in the transport from endoplasmic reticulum to Golgi); Trafficking protein particle complex 4 (TRAPPC4) (involved in the transport from endoplasmic reticulum to Golgi, vesicular transport, dendritic morphogenesis, biosynthesis of neurotransmitter receptors); Trafficking protein particle complex 5 (TRAPPC5); Trafficking protein particle complex 6 (TRAPPC6).

Example 6

Functional Characterization of the RCC BA85#21 Clone by Microarray—Immunogenicity The immunogenicity of the RCC BA85#21 clone was assessed, after in vitro stimulation of autologous lymphocytes by MLTC (mixed lymphocyte-tumor cell cultures), by means of the Elispot technique to measure IFN-γ release from antigen specific CD8 lymphocytes, and by cytotoxicity tests, associated with $^{51}$Cr release, with which the ability of said activated lymphocytes to lyse clonal tumor cells was measured.

Initially, the PBMCs of the same patient as RCC BA85#21 were activated by co-incubation with the RCC tumor cells previously stimulated with INF-γ (100 IU/ml) for 48 hours (autologous system). The cells were then seeded into 24-well plates in a "responder/stimulator" (PBMC/RCC BA85#21) ratio of 10:1 and maintained in AIM-V (Invitrogen) culture medium with added 5% human serum and IL-2 (250 IU/ml). Then, $1\times10^6$ PBMC (responders) were co-incubated with $1\times10^5$ RCC BA85#21 cells (stimulators) previously irradiated with 10,000 rads. One week later and then for two successive weeks, the lymphocytes were again stimulated with RCC BA85#21 cells in culture medium with added IL-2 (250 IU/ml).

Three weeks after initiation of in vitro stimulation ($T_{21}$) the $CD8^+$ lymphocytes were isolated using immunomagnetic microbeads (Milteny Biotech). On the $35^{th}$ day ($T_{35}$) the $CD8^+$ T-cell "responders" were stimulated for a further two weeks with the previously irradiated RCC BA85#21 clone.

The antigen-specific cells and degree of immunogenicity were tested against RCC BA85#21 in both the presence and absence of anti HLA-I monoclonal antibodies by the Elispot technique (Herr W et al. J Immunol Methods. 1997 Apr. 25; 203(2):141-52).

The Elispot assay enabled the extent of INF-γ release by $CD8^+$ T-lymphocytes to be evaluated as 330 INF-γ$^+$ cells out of 10,000=3.3%. In the immunology field this value is very high. INF-γ release was inhibited by 91% by the monoclonal antibody directed against Class I antigens, confirming the immunogenicity of the RCC BA85#21 clone and the antigen-specific response induced by the clone itself.

The cytotoxicity and $^{51}$Cr release test was undertaken following standard methodology (Dorrschuck A et al, Blood, 2004 Oct. 15; 104(8):2591-9). In brief, one million tumor cells were incubated for 75 minutes at 37° C. with $^{51}$Cr (200 µCi/ml). The cells thus labelled were washed three times and re-suspended in RPMI 1640 with 10% FCS. The lymphocytes (responders) were diluted in duplicate in a 96-well plate in target/responder ratios of 90:1, 30:1, 10:1, 3:1, 1:1. The labelled tumor cells were added to the T-lymphocyte responders at a concentration of 1000 cells/well. The cells thus plated were incubated for 5 hours at 37° C. At the end of the incubation the plate was centrifuged at 200 g for 5 minutes and 80 µl of the supernatant were collected to be counted in the gamma counter.

The results are shown in FIG. 3: the cytotoxic $CD8^+$ lymphocytes (CTL) efficiently lysed cells of the RCC BA85#21 clone (60%, E/T ratio=30:1), but not the erythroid line K565 used to assess non-specific cytotoxicity (<20%, E/T ratio 60:1). The combined phenotypical and functional characterization data confirmed the presence of integrin ICAM-1 (CD54), co-stimulatory CD40 molecule and HLA-I molecules, able to present tumor antigens. Therefore the RCC cell line therefore is able to induce a class I and immunogenic response.

This fact was confirmed from the results of the co-culturing of the cell clone with autologous T-lymphocytes. In particular the Elispot assay confirmed that the RCC BA85#21 line was able to induce INF-γ release by activated CD8 lymphocytes with a class I response (91%) while the cytotoxicity test confirmed that said activated lymphocytes were able to specifically lyse the RCC BA85#21 cell line (60%, E/T ratio: 30:1) used for the stimulation.

The combined functional and phenotypical data therefore show the increased immunogenicity of the RCC BA85#21 line and its usefulness in therapy for the treatment of patients affected by clear cell renal carcinoma.

The invention claimed is:

1. A cell line of clear cell renal carcinoma RCC BA85#21A, deposited as number PD04006 at the CBA (advanced biotechnology Center), Genoa-Italy, wherein said cell line comprises loss of heterozygosity (LOH) at the DP1 (D5S346) locus.

2. The cell line as claimed in claim 1 transformed with heterologous nucleic acids.

3. The cell line as claimed in claim 1 activated by cytokines or antibodies.

4. A lysate and/or apoptotic bodies of the cell line as in claim 1.

5. A protein fraction of the lysate of claim 4.

6. A Composition comprising cells of the RCC BA85#21 cell line claim 1, in combination with suitable excipients and/or diluents.

7. A Composition comprising one or both of the lysate and the apoptotic bodies of claim 4, in combination with suitable excipients, diluents, or adjuvants.

8. A method for producing cells of the immune system capable of specifically recognizing clear cell renal carcinoma, comprising co-incubating immune cells selected from the group consisting of lymphocyte cells and dendritic cells with cells of the RCC BA85#21 cell line as in claim 1 or derivatives thereof, wherein said derivatives comprise one or both of a lysate and apoptotic bodies and wherein said co-incubating is done in a culture medium until renal carcinoma antigen-specific cells are obtained.

9. The method of epi claim 8 wherein said lymphocytes are CD4+ and/or CD8+.

10. The method of claim 8 wherein the renal carcinoma antigen specificity of said cells of the immune system is evaluated by one or more methods selected from the group consisting of: flow-cytometry, cell proliferation, production of cytokines, and antigen markers.

11. A kit comprising the RCC BA85#21 cell line as in claim 1 or derivatives thereof in combination with reagents suitable for preparation of a composition selected from the group consisting of vaccine composition and immunogenic composition, wherein said derivatives comprise one or both of a lysate and apoptotic bodies.

12. The kit as in claim 11 wherein the cell line or derivatives thereof are in selected from the group consisting of frozen, lysate, and lyophilizate.

13. The cell line of claim 1, wherein said cell line lacks the microsatellite instability (MSI) marker.

* * * * *